(12) United States Patent
Karasiuk et al.

(10) Patent No.: US 8,128,638 B2
(45) Date of Patent: Mar. 6, 2012

(54) HANDHELD MICRODERMABRASION DEVICE

(75) Inventors: Kenneth B Karasiuk, Oak Park, CA (US); N. Brendon Boone, III, Encino, CA (US); Steven Edward Wojcik, Shoreline, WA (US)

(73) Assignee: eMed, Inc., Westlake Village, CA (US)

( * ) Notice: Subject to any disclaimer, the term of this patent is extended or adjusted under 35 U.S.C. 154(b) by 331 days.

(21) Appl. No.: 11/897,229

(22) Filed: Aug. 28, 2007

(65) Prior Publication Data

US 2009/0062815 A1   Mar. 5, 2009

(51) Int. Cl.
*A61B 17/50* (2006.01)

(52) U.S. Cl. ....................................... 606/131

(58) Field of Classification Search ............ 451/87, 451/89–91, 94; 604/35–37, 289–290, 313, 604/317, 319, 321; 606/131; 132/73, 73.6, 132/74.5, 75.6, 75.8, 76.4; 433/125, 142, 433/166

See application file for complete search history.

(56) References Cited

U.S. PATENT DOCUMENTS

| | | | | |
|---|---|---|---|---|
| 2,714,788 | A | * | 8/1955 | Tigellia .................... 451/359 |
| 5,309,590 | A | | 5/1994 | Giuliani et al. |
| 5,476,384 | A | | 12/1995 | Giuliani et al. |
| 5,733,261 | A | * | 3/1998 | Obong ..................... 604/110 |
| 5,971,999 | A | | 10/1999 | Naldoni |
| 6,140,802 | A | | 10/2000 | Lundell et al. |
| 6,162,232 | A | | 12/2000 | Shadduck |
| 6,220,772 | B1 | | 4/2001 | Taylor |
| 6,241,739 | B1 | | 6/2001 | Waldron |
| 6,287,289 | B1 | * | 9/2001 | Niedospial, Jr. ........... 604/408 |
| 6,299,620 | B1 | | 10/2001 | Shadduck et al. |
| 6,387,103 | B2 | | 5/2002 | Shadduck |
| 6,402,410 | B1 | | 6/2002 | Hall et al. |
| 6,500,183 | B1 | | 12/2002 | Waldron |
| 6,575,203 | B2 | | 6/2003 | Hall et al. |
| 6,629,983 | B1 | | 10/2003 | Ignon |
| 6,641,591 | B1 | | 11/2003 | Shadduck |
| 6,644,878 | B2 | | 11/2003 | Hall et al. |
| 6,695,853 | B2 | | 2/2004 | Karasiuk |
| 6,808,331 | B2 | | 10/2004 | Hall et al. |
| 6,911,031 | B2 | * | 6/2005 | Muldner ................... 606/131 |
| 6,942,649 | B2 | * | 9/2005 | Ignon et al. .............. 604/289 |
| 7,238,165 | B2 | * | 7/2007 | Vincent et al. ........... 604/6.11 |
| 2002/0016601 | A1 | | 2/2002 | Shadduck |
| 2004/0138680 | A1 | | 7/2004 | Twitchell et al. |
| 2004/0143274 | A1 | | 7/2004 | Shadduck |

OTHER PUBLICATIONS

Shah, Sachin A. et al., Delivery of esomeprazole magnesium through nasogastric and gastrostomy tubes using an oral liquid vehicle as a suspending agent in vitro, Oct. 1, 2006, American Society of Health-System Pharmacists, Inc., vol. 63, p. 1883.*

* cited by examiner

*Primary Examiner* — Ryan Severson
*Assistant Examiner* — Ashley Cronin
(74) *Attorney, Agent, or Firm* — Fountainhead Law Group P.C.

(57) ABSTRACT

In one embodiment, a handheld microdermabrasion device includes a treatment head and a motor for driving, e.g., oscillating or rotating, the treatment head to abrade or exfoliate the skin. The treatment head may be abrasive or non-abrasive, and includes a passage or opening in communication with a reservoir for containing a topical solution. As the skin is abraded by the treatment head, the topical solution from the reservoir is automatically dispensed through the opening in the treatment head. In some embodiments, the motor which drives the treatment head also drives a pump for moving fluid from the reservoir and through the treatment head. The topical solution may be abrasive or non-abrasive. In some embodiments, the topical solution is a therapeutic solution for treating the skin.

21 Claims, 7 Drawing Sheets

HANDHELD MICRODERMABRASION DEVICE

BACKGROUND

The present invention relates to skin treatment and conditioning, and in particular, to handheld devices and methods for microdermabrasion.

Microdermabrasion is a process for removing dead cells from the outermost layer of the skin (the epidermis) to provide a younger and healthier looking appearance, remove wrinkles, clean out blocked pores, remove some types of undesirable skin conditions that can develop, and enhance skin tone. The process of microdermabrasion must be performed with a certain degree of accuracy, so that underlying live layers of skin tissue are not removed or damaged, but that enough dead cells are removed to give effective results.

Various devices and techniques for microdermabrasion have been used. For example, some devices utilize a brush for removing skin blemishes which includes rotating metallic bristles. Such a device is more properly referred to as a dermabrasion device as it is quite aggressive in the amounts and rates of tissues removed. While this type of device can be effective for removing gross scarring and keloids such as those associated with burn victims, it can also cause scarring and is difficult to accurately control with regard to amounts of tissue removed. As such it is not effective for performing microabrasion.

U.S. Pat. No. 6,695,853 discloses an improved microdermabrasion system which utilizes a treatment head and a external vacuum system to draw fluids through the treatment head using an extended tubing arrangement between the treatment head and external vacuum system. The fluids are delivered to the skin during exfoliation by the treatment head, and excess fluid and abraded cells are taken up by the vacuum system to an external waste collection system through more extended tubing. While such systems and methods improve over prior systems and may be effective for exfoliating the skin while delivering a topical solution to the skin, it is not self-contained and may not be suitable for simple, regular hand-held use by individual patients or users.

Thus, there remains a need for a more compact, handheld microdermabrasion device that is easy to operate and is suitable for regular use by individuals.

SUMMARY

Embodiments of the present invention improve microdermabrasion. In one embodiment the present invention includes a motor-driven treatment head with an abrasive surface which contacts the section of skin to be treated. The treatment head includes a passage or opening in communication with a reservoir for containing a topical solution. As the skin is treated, the topical solution from the reservoir is automatically dispensed through the opening in the treatment head. The topical solution may be abrasive or non-abrasive. In some embodiments, the topical solution is a therapeutic solution for treating the skin.

In one embodiment, the present invention includes a handheld microdermabrasion device, comprising an abrading member for abrading the skin of a user, a drive system, said drive system coupled with said abrading member and configured to drive movement of the abrading member, a fluid delivery system fluidly connected to an interface between the abrading member and the skin of a user, a power source in electrical communication with said drive system for activating said drive system, and a housing having at least one wall containing said fluid delivery system, said drive system, and said power source, wherein said abrading member extends outward from the at least one wall, wherein the fluid delivery system contains a skin treatment fluid, and said skin treatment fluid is delivered to the interface between the abrading member and the skin of a user.

In one embodiment, the fluid delivery system comprises a pump.

In one embodiment, the device further comprises an input port communicating with said pump.

In one embodiment, the device further comprises a container removably coupled with the input port.

In one embodiment, the container comprises a wall surrounding a central cavity for containing said material.

In one embodiment, the container wall comprises a plastic sheet, a metal foil, or a combination thereof, and is at least partially collapsible as said material is dispensed from the container.

In one embodiment, said container contains skin treatment fluid.

In one embodiment, the fluid delivery system comprises a syringe and a spring mechanism abutted to the syringe, and wherein the spring mechanism comprises a compressed state and an uncompressed state.

In one embodiment, the syringe comprises a plunger and a syringe chamber filled with said skin treatment fluid.

In one embodiment, the plunger is abutted to the spring mechanism.

In one embodiment, the syringe chamber is filled with an air pocket having a volume greater than the volume of a tube coupled between the syringe and the abrading member.

In one embodiment, said drive system comprises a motor.

In one embodiment, said drive system further comprises one or more gears for driving the movement of the abrading member.

In one embodiment, said drive system further comprises a spindle coupled with said abrading member and pivotably attached within said housing, said spindle for guiding the movement of the abrading member.

In one embodiment, said drive system further comprises a crankshaft having a proximal end coupled with the gears and a distal end slidably engaged within a slot in the spindle, wherein rotating the crankshaft slides the distal end of the crankshaft within the slot and moves the abrading member in a defined pattern.

In one embodiment, said motor is configured to drive said fluid delivery system to deliver the skin treatment fluid to an interface between the skin of a user and the abrading member.

In one embodiment, a guard ring laterally surrounding said abrading member.

In one embodiment, said abrading member comprises an annulus including a central opening coupled to said fluid delivery system for passing a skin treatment fluid therethrough.

In another embodiment, the present invention includes a method of performing microdermabrasion comprising applying an abrading member of a handheld microdermabrasion device to a skin surface, said microdermabrasion device including a power supply, a fluid delivery system, and a drive system coupled with the abrading member and disposed within a housing, oscillating the abrading member over the skin surface using the drive system, and applying a skin treatment solution from the fluid delivery system within the microdermabrasion device to the skin.

In one embodiment, said applying further comprises attaching a container to an input port of a pump, and actuating the pump using the drive system to pump the skin treatment solution from the container, through a tube connected to the pump within the housing, and through an opening in the abrading member.

In one embodiment, said applying further comprises attaching a syringe between a spring mechanism and a tube, the syringe comprising a syringe chamber filled with said skin treatment fluid, and actuating the spring mechanism to force the skin treatment fluid from the syringe chamber, through the tube, and to an interface between the skin of a user and the abrading member.

In one embodiment, a handheld microdermabrasion device comprises an abrading member having one or more openings for passing a material therethrough and a drive system including a motor, a pump, a power supply, and a housing having at least one wall containing the motor, pump, and power source, and wherein the abrading member extends outward from at least one wall. The drive system is coupled with the abrading member and configured to drive movement of the abrading member; the pump is fluidly connected with the one or more openings of the abrading member for passing a material from a container through the one or more openings; the power supply is in electrical communication with the motor for activating said motor. In some embodiments, the device may further include a guard ring surrounding the abrading member. The abrading member, with or without the guard ring, is sometimes referred to herein as a "treatment head". Other configurations or types of treatment heads may be employed.

In some embodiments, the handheld microdermabrasion device further comprises an input port communicating with the pump, said input port configured to removably couple with the container. In some embodiments, the device comprises the container with or without a topical solution contained therein. The topical solution may be any of a fluid, liquid, semi-liquid, lotion, paste, cream, gel, powder, or any combination thereof, and may or may not contain abrasive particles. In some embodiments, the container comprises a wall surrounding a central cavity for containing the topical solution and a coupler for removably attaching with the input port. The container wall may comprise a plastic sheet, a metal foil or a combination thereof, and can be at least partially collapsible as the topical solution is dispensed from the container.

In some embodiments drive assembly further comprises one or more gears for driving the movement of the abrading member. The drive assembly may further comprise a spindle coupled with the abrading member and pivotably attached within the housing, wherein the spindle is for guiding the movement of the abrading member. The drive assembly may further comprise a crankshaft having a proximal end coupled with the gears and a distal end slidably engaged within a slot in the spindle, wherein rotating the crankshaft slides the distal end of the crankshaft within the slot and moves the abrading member in a defined pattern, for example an oscillatory pattern or any other desired pattern. In some embodiments, the gears are configured to drive the pump to deliver the material from the container and through the one or more openings of the abrading member.

In some embodiments, the housing of a handheld microdermabrasion device comprises a removable access cover for accessing a container of topical solution and/or other elements of the device. The housing may further include a main housing and an electrical sub-housing, wherein the electrical sub-housing substantially encloses the motor and the power supply and is configured to removably attach to the main housing. The drive system may further comprise a first coupling member and a second coupling member, said first coupling member attached to a distal portion of the drive system and disposed within the main housing and said second coupling member disposed within the electrical subhousing and attached with the motor, wherein the second coupling member engages with the first coupling member through an access hole in the main housing when said electrical subhousing attaches to the main housing. In some embodiments, the power supply comprises at least one battery contained within said electrical subhousing.

A method of performing microdermabrasion according to one embodiment of the invention comprises applying an abrading member of a handheld microdermabrasion device to a skin surface, said microdermabrasion device including a power supply, a pump and a drive system coupled with the abrading member and disposed within a housing; oscillating the abrading member over the skin surface using the drive system; and applying a topical solution from a container within the microdermabrasion device through the pump and to the skin surface through an opening in the abrading member. In some embodiments, said applying further comprises attaching a container to an input port of the pump, and actuating the pump using the drive system to pump the topical solution from the container, through a tube connected to the pump within the housing, and through an opening in the abrading member.

The following detailed description and accompanying drawings provide a better understanding of the nature and advantages of the present invention.

DETAILED DESCRIPTION

Described herein are apparatus and techniques for microdermabrasion. In the following description, for purposes of explanation, numerous examples and specific details are set forth in order to provide a thorough understanding of the present invention. It will be evident, however, to one skilled in the art that the present invention as defined by the claims may include some or all of the features in these examples alone or in combination with other features described below, and may further include modifications and equivalents of the features and concepts described herein.

Figure 1A:
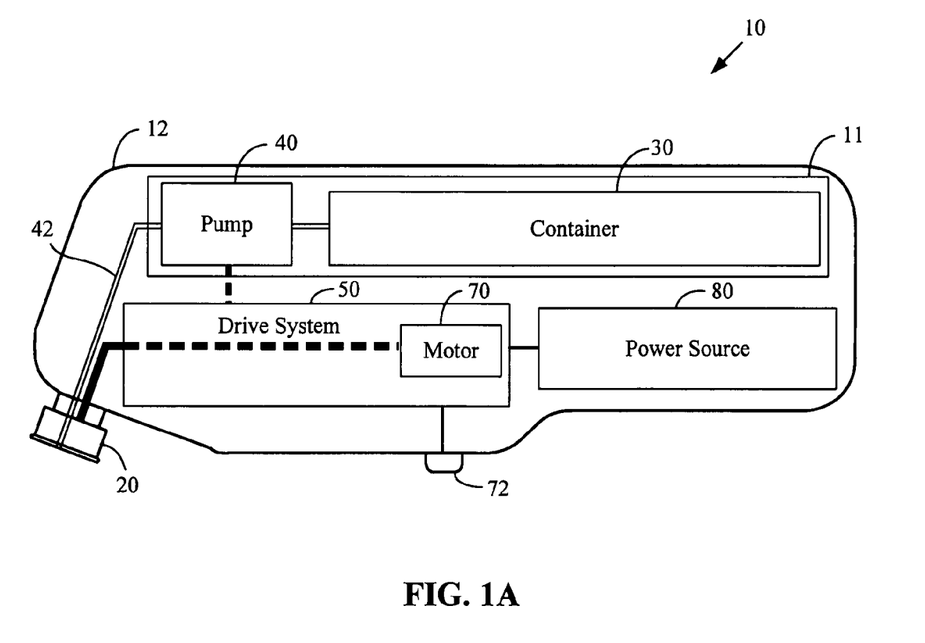
FIG. 1A is a schematic diagram of a handheld microdermabrasion device according to one embodiment of the present invention.

FIG. 1A is a schematic side view illustration of a handheld microdermabrasion device 10 according to an embodiment of the present invention. Device 10 includes a treatment head 20 including an abrading member having an abrasive surface for abrading the skin of a user, a drive assembly system 50 for driving the treatment head 20 to abrade the skin of the user, and a fluid delivery system 11. As described in the examples below, the abrading member may have one or more openings, such as an annular shape, with a tube 42 coupled to the opening(s) to deliver skin treatment fluids. However, it is to be understood that a variety of abrasive members may be used that do not have openings, wherein fluids may be delivered to the skin interface proximate to (i.e., near) the abrasive member. The drive system 50 may be coupled with the treatment head 20. In one example embodiment described in more detail below, the drive system 50 comprises an electric motor 70. However, it is to be understood that a variety of electromechanical devices (e.g., devices that translate electricity into mechanical action or movement) may be used for drive system 50. A power source 80 may be used to provide power to the drive system 50. In one embodiment, the power source is an internal power source (e.g., batteries), and in another embodiment the handheld device may be coupled to an external power source (e.g., a wall power outlet).

In this example, the fluid delivery system 11 comprises a pump 40 and container 30. Pump 40 may communicate with a container 30 and the treatment head 20 to dispense the topical solution from the container 30 and to the treatment head 20. In one embodiment, container 30 is a refillable container. In another embodiment, container 30 is a replaceable container. In some embodiments, the drive system 50 may be coupled with the fluid delivery system (e.g., pump 40) such that activation of the drive system 50, e.g., using a switch 72, actuates the fluid delivery and moves the treatment head 20, e.g., in an oscillating motion. A housing 12 may substantially surround one or more of the pump 40, the drive system 50, the power source 80 and/or the container 30. Treatment head 20, may extend from housing 12 such that an abrasive surface of treatment head 20 may be applied to the skin of the user while the user holds the device 10 by the housing 12.

Figure 1B:
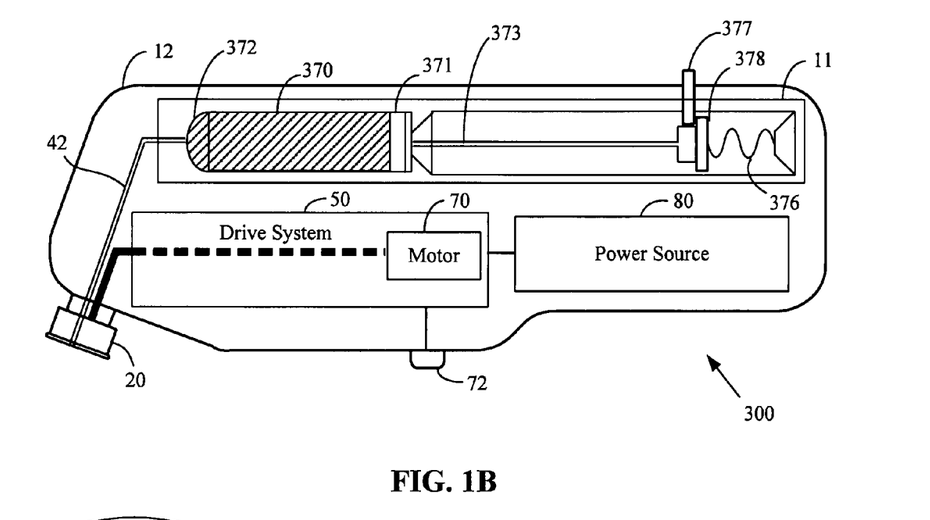
FIGS. 1B-C are schematic diagrams of a handheld microdermabrasion device according to one embodiment of the present invention.
Figure 1C:
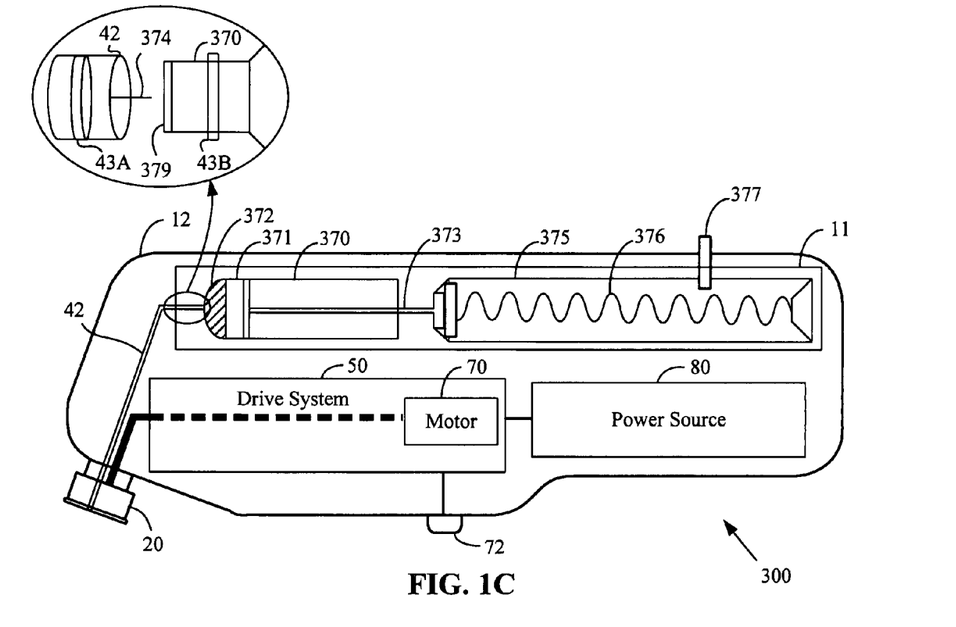

FIGS. 1B-C illustrates a schematic side view of a handheld microdermabrasion device 300 according to an embodiment of the present invention. Device 300 includes a treatment head 20 including an abrading member having an abrasive surface for abrading the skin of a user, a drive system 50 for driving the treatment head 20 to abrade the skin of the user, a fluid delivery system 11, and a power source 80. In this example, the fluid delivery system 11 comprises a spring loaded syringe mechanism including a syringe comprising syringe chamber 370 and a plunger 373 coupled to a spring mechanism 375. For example, a variety of skin treatment fluids may be provided in pre-filled syringes, and the syringes may be placed in the handheld device and actuated by a spring. Syringe chamber 370 may contain a topical solution for application to the skin of a user during the abrading of the skin. Spring mechanism 375 provides a force to plunger 373 for pumping the topical solution from the syringe chamber 370.

Delivery of the topical solution may start with the removal of a housing 12 from the device to load a new syringe filled with topical fluid and to reset the spring mechanism 375. The user may compress the spring mechanism until it locks into place with release lever 377. This is known as the compressed state. FIG. 1B illustrates the spring mechanism in the compressed state with release lever 377 securing the mechanism in the compressed state. In the compressed state, the spring mechanism has stored energy that may be used at a later time. In one embodiment, spring mechanism 375 comprises spring 376. Compression of the spring 376 stores potential energy which may later be used to distribute the topical solution. Once the spring mechanism 375 has entered a compressed state, a new syringe may be placed within the device. Syringe chamber 370 may be pre-filled topical solution 372 and may include an air pocket 371 as described below. The syringe is placed within the device with the plunger 373 abutting the spring mechanism end 378. To activate the delivery of the topical solution, the release lever 377 is released. During the transition of the spring mechanism from the compressed state to the uncompressed state, the stored energy within the spring mechanism 375 may cause the spring mechanism to exert pressure on the plunger 373 and deliver fluid to tube 42.

One example coupling between the syringe and tube 42 is illustrated in FIG. 1C. Tube 42 may include a needle 374. A new pre-filled fluid container such as a syringe chamber 370 may have a first end having a radius less than the radius of the tube 42 so that the end of the syringe chamber may enter the tube. The end of the syringe may be sealed with a thin sheet of material such as plastic or aluminum, for example, and when the end of the syringe is placed within tube 42, a needle 374 may puncture the thin material and allow the fluid in the syringe to enter the tube 42. It may be desirable to recess the needle within the tube to prevent injuries. The radius of the tube 42 may be only slightly larger than the radius of the end of the syringe allowing for a secure coupling so that no fluid is transmitted outside of the tube-syringe interface. One or more "O-rings" 43A in the tube or 43B on the syringe (or both), for example, may also be used to ensure a fluid tight seal. When needle 374 punctures syringe 370, topical solution 372 stored within the syringe may flow into tube 42. The end of tube 42 is coupled to the treatment head 20 for delivery of the topical solution 372 to the skin of the user. In one embodiment, the needle 374 may be removed, allowing syringe 370 to be directly coupled to tube 42. If the viscosity of the treatment fluid is low, the end of the syringe may be covered with a removable cap rather than a thin material because the fluid may not be as apt to flow out during replacement.

As the energy stored in the spring mechanism 375 applies pressure on the plunger 373, topical solution 372 may flow through tube 42. In one embodiment, the flow of the topical solution 372 is a controlled based on the viscosity of the topical solution 374, the circumference of the tube 42 or needle 374 (or both), and the energy output of the spring. In other embodiments, tube 42 may be constricted to further restrict the flow of the topical solution 372. Once the topical solution 372 is completely exhausted, the air pocket 371 enters the tube 42 to expel any residual solution remaining in the device. This may contribute in keeping the device clean for future use. The volume of air included in the syringe or any other fluid delivery system may be greater the volume of the tube 42 to reduce the amount of fluid retained in the device after the fluid chamber is empty.

Figure 2A:
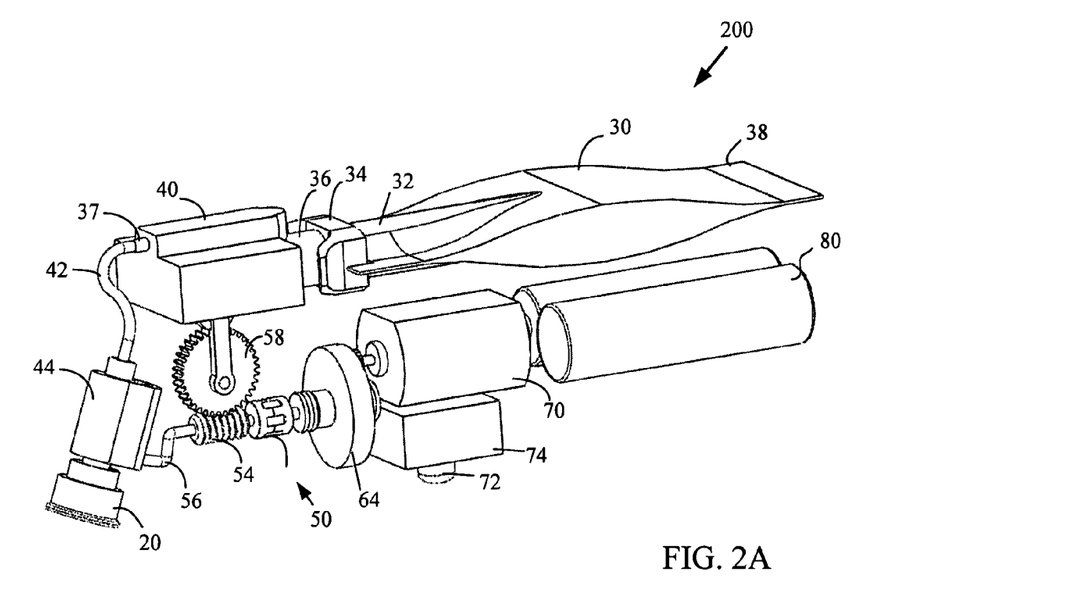
FIGS. 2A and 2B are perspective view illustrations of an embodiment of the microdermabrasion device of FIG. 1.

FIG. 2A is a perspective side view illustration of a handheld microdermabrasion device 200 according to one embodiment of the present invention. Device 200 includes a treatment head 20, a container 30 for dispensing a topical solution, and a drive assembly 50 for driving the treatment head 20 to abrade the skin of a user. In some embodiments, a pump 40 communicates with the container 30 and the treatment head 20 to dispense a topical solution from the container 30 through the treatment head 20. For example, pump 40 may include a first coupler or port 36 for connecting with and receiving solution from container 30, and a second coupler or port 37 for coupling with a tube 42 that communicates with the treatment head 20 through a spindle 44 or other member for securing treatment head. In some embodiments, drive assembly 50 includes a motor 70 and, in use, drives movement of the treatment head 20 and actuates pump 40 to deliver material from container 30 to and through treatment head 20.

A switch 72 or other device may be used to activate motor 70. Pump 40 and drive assembly 50, and associated gearing and other elements, are discussed in greater detail below with respect to FIG. 3.

Figure 2B:
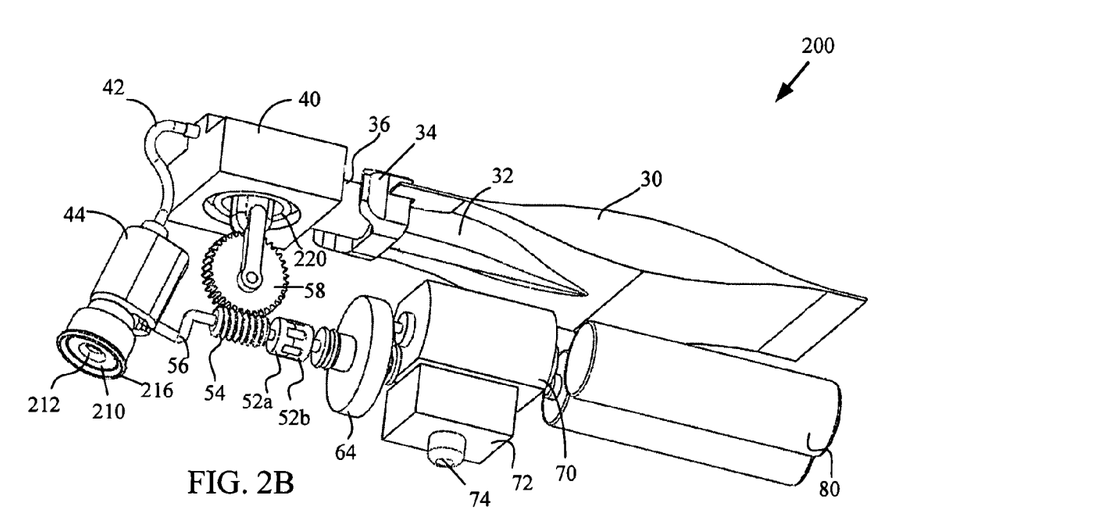

As shown in the perspective bottom view illustration of FIG. 2, treatment head 20 of exemplary device 200 comprises an abrading member 210 configured and dimensioned to provide contact with and abrade the skin when treatment head is moved over the skin, e.g., by oscillating, vibrating, rotating, or any other manner of movement of the treatment head over the skin. Abrading member 210 is preferably annular, having a lumen or passage 212 through which topical solutions or other materials may pass. Passage 212 is preferably in fluid communication with pump, e.g., through spindle 44 and tube 42. Tube 42 is preferably, although not necessarily, at least partially flexible and may be made of PVC or other compatible plastic, for example.

In some embodiments, treatment head 20 may further comprise a guard ring 216 surrounding abrading member 210 which helps confine topical solution or other materials to the area covered by the treatment head. The abrading member 210 may be recessed relative to an outer edge 216 of the guard ring to help reduce the contact pressure between abrading member 210 and the skin. In one example, abrading member 210 is recessed a fixed amount, optimally between 0.5 to 1 mm. In another example, abrading member 210 is recessed an adjustable amount therefore making it adaptable to differences in skin types (e.g., men's skin women's skin, age of skin) and/or conditions (e.g., irregularities in the skin related to this specific user). Moreover, guard ring 216 may be at least partially flexible or resilient to allow a user to increase or decrease contact pressure between abrading member and the skin by varying the amount of force used to press treatment head against the skin. Guard ring 216 may be made of any material that provides desired properties, e.g., PVC or other plastic materials.

Abrading member 210 may have abrasive particles fused to its surface, or could alternatively be made as an abrasive disk and fitted within an open end of the treatment head. Although the outer surface of abrading member 210 shown is substantially planar, it may alternatively be rounded, flared, concave, convex or elongated, for example. The abrasive particles may be of a size ranging from about 50 to 300 grit, typically about 100 to 120 grit and are typically corundum (aluminum oxide), sodium bicarbonate, magnesium oxide, silicone carbide, or sapphire, or the like. The coarser particles (at the lower ends of the grit ranges) may be provided on an abrasive member for use in initial treatments, while finer particles (at the higher ends of the grit ranges) may be employed for subsequent treatments. Alternatively, the abrading member may be formed by knurling, machining, laser treatment or other mechanical or chemical treatment. In some embodiments, abrading member 210 may have any of the characteristics as the treatment tips described in U.S. Pat. No. 5,971,999 (which is hereby incorporated in its entirety by reference thereto)

As used herein, the term topical solution is intended to comprise any abrasive or non abrasive material, e.g. a fluid, liquid, semi-liquid, lotion, paste, cream, gel, powder, or any combination thereof. In some embodiments, the topical solution may be any material or solution for treating skin, and may comprise any suitable therapeutic agent, e.g. vitamins, medicines, moisturizers, skin conditioners, sunscreens, etc.

In alternative embodiments, container 30 may include a topical solution having abrasive particles, such as corundum crystals, sodium bicarbonate particles or other abrasive particles, including those disclosed in U.S. Pat. No. 5,971,999, to perform a microabrading function. If used, the abrasive particles may be used together with any of the fluids mentioned above or with some other fluid carrier medium, such as those described in U.S. Pat. No. 5,971,999, for example. In embodiments utilizing a topical solution containing abrasive particles, abrading member 210 may be substantially smooth or non-abrasive.

Container 30 may be constructed of any material or combination of materials that permit the container to be at least temporarily collapsed, squeezed, compressed or otherwise manipulated to expel its contents. For example, the container may have the form of a collapsible or semi-collapsible tube as illustrated in FIGS. 1 and 2, and/or may be readily extruded, molded, thermoformed or otherwise formed from any appropriate material, such as for example, plastic, metal, glass or any combination thereof. In some embodiments, container 30 comprises a synthetic plastic material, such as for example polyethylene, polyvinyl, polypropylene, polyethylene terephthalate or polyvinyl chloride. In other embodiments the container 30 may be fabricated from one or more layers of synthetic plastic and/or other materials, such as for example, thin metals including aluminum, tin, lead, or the like. Container may include one or more seals 38, e.g., a crimp seal, heat seal or adhesive seal. In other embodiments, container 30 may be any open or closed container for storing and/or expelling a material, including but not limited to a bag, a pouch, a vial, a cartridge or a chamber. In certain embodiments container 30 is a syringe or other device for storing and expelling a topical solution. In some embodiments, container 30 is refillable.

Figure 3:
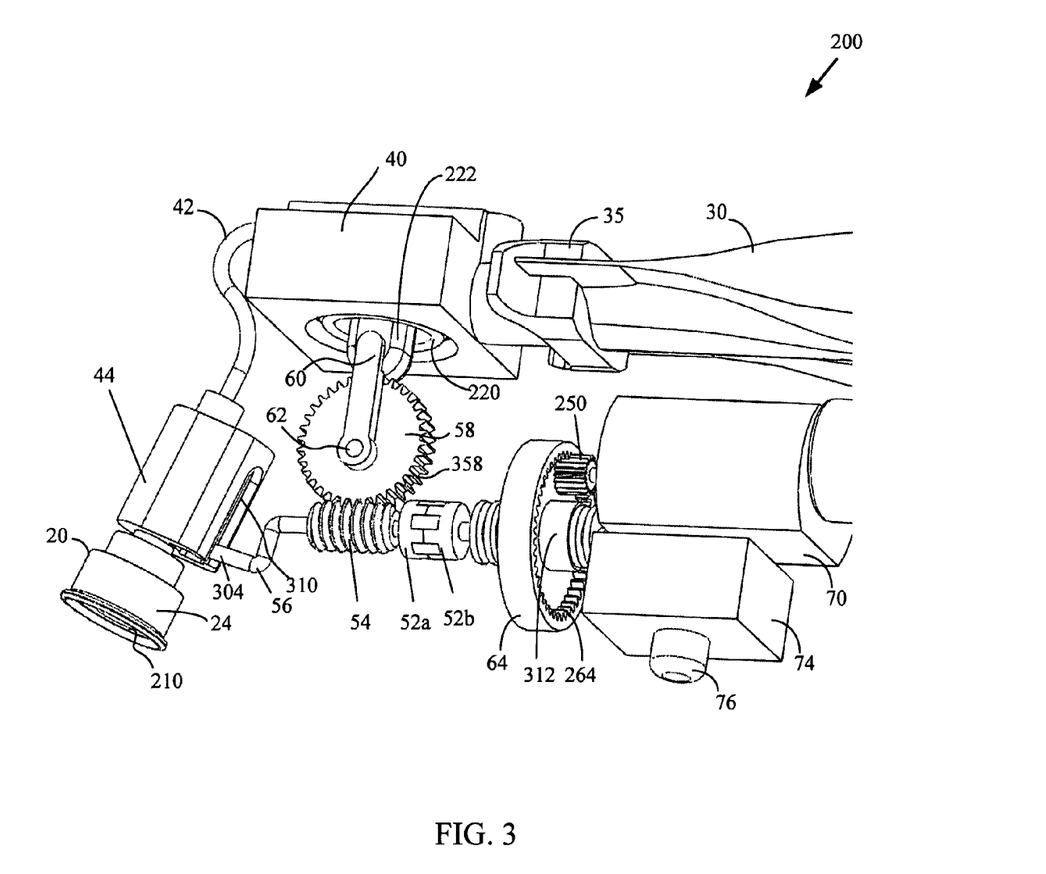
FIG. 3 is a close-up perspective view illustration of the microdermabrasion device of FIGS. 2A and 2B.

Container 30 may include any number of features which facilitate attachment and/or use within device 200. For example, container 30 may include a coupler 34 configured and dimensioned to receive or otherwise sealingly connect with pump 40, e.g. through port 36 as shown in FIG. 1. Preferably, the connection between container 30 and pump 40 is removable, such that container may be easily removed and replaced by a user. Coupler 36 may further include one or more extended features 35, as shown in FIG. 3, to facilitate handling by a user during connection and/or removal of the container 30. A substantially rigid neck 32 may further facilitate connection to device 200 and prevent port 36 from becoming inhibited or blocked as container 30 collapses when contents are expelled.

A power source 80, e.g., here shown as a pair of batteries, may be included to provide power for drive assembly 50 and/or pump 40. One skilled in the art will appreciate that the batteries 80 illustrated in FIG. 1 are merely illustrative, and that any number or type of batteries or other power source may be used. In some embodiments, power source 80 may be rechargeable. In other embodiments, power source 80, also referred to herein as power supply 80, may be connectable to an external power supply during recharging and/or during use. In other embodiments, no power source is used and movement of the treatment head and/or dispensing of material from container is performed manually.

An exemplary drive assembly 50 for driving movement of treatment head 20 and/or pump 40 of device 200 will now be discussed with reference to FIGS. 1-3. In particular, components of drive assembly 50 and pump 40 are shown in greater detail in the close-up illustration of FIG. 3. In this embodiment, motor 70 is coupled to treatment head 20 through reducing gearing 250 and 64 to reduce the output speed of the motor and increase torque for driving the treatment head. Drive gear 250 engages teeth 264 of gear 64, which is preferably larger than gear 64 and has an axis of rotation 312 that is offset from that of drive gear 250 as shown in FIG. 3. Of course, various other reduction gears and/or other mechanisms for imparting a desired force or torque to drive treatment head are known and may be employed. The output of reduction gears 64, 250 may be transmitted through a selectively engageable coupling 52, including coupling members 52a and 52b, to permit motor 70, power supply 80, and/or other components to be detached to facilitate cleaning of the treatment head 20 portion of device 200.

Coupling 52a, 52b is attached to a crankshaft 56 as motor 70 turns gears 250 and 64. A distal portion 304 of crankshaft 56 is offset and angled with respect to proximal portion 302, and is slideably engaged in an elongated slot 310 of spindle 44. As crankshaft 56 rotates, distal portion 304 slides in a reciprocating fashion within slot, causing spindle 44 to oscillate in a defined pattern. Treatment head 20, including abrading member 210 in this example, is attached to spindle 44 and oscillates with spindle 44 to provide an abrading motion when member 210 contacts skin In this example, spindle 44 oscillates through an angle of about 30 degrees (+or − about 15 degrees). In other embodiments, spindle oscillates any desired angle, for example between about 5 degrees and 60 degrees, more preferably between about 15 degrees and about 45 degrees. In some embodiments, drive assembly 50 may be configured to oscillate, rotate or otherwise move treatment head in any desired manner or degree. In embodiments including a guard ring 216 around abrading member 210, abrading member 210 may be configured to move independently of guard ring 216 using drive and gearing mechanisms, for example.

Figure 4:
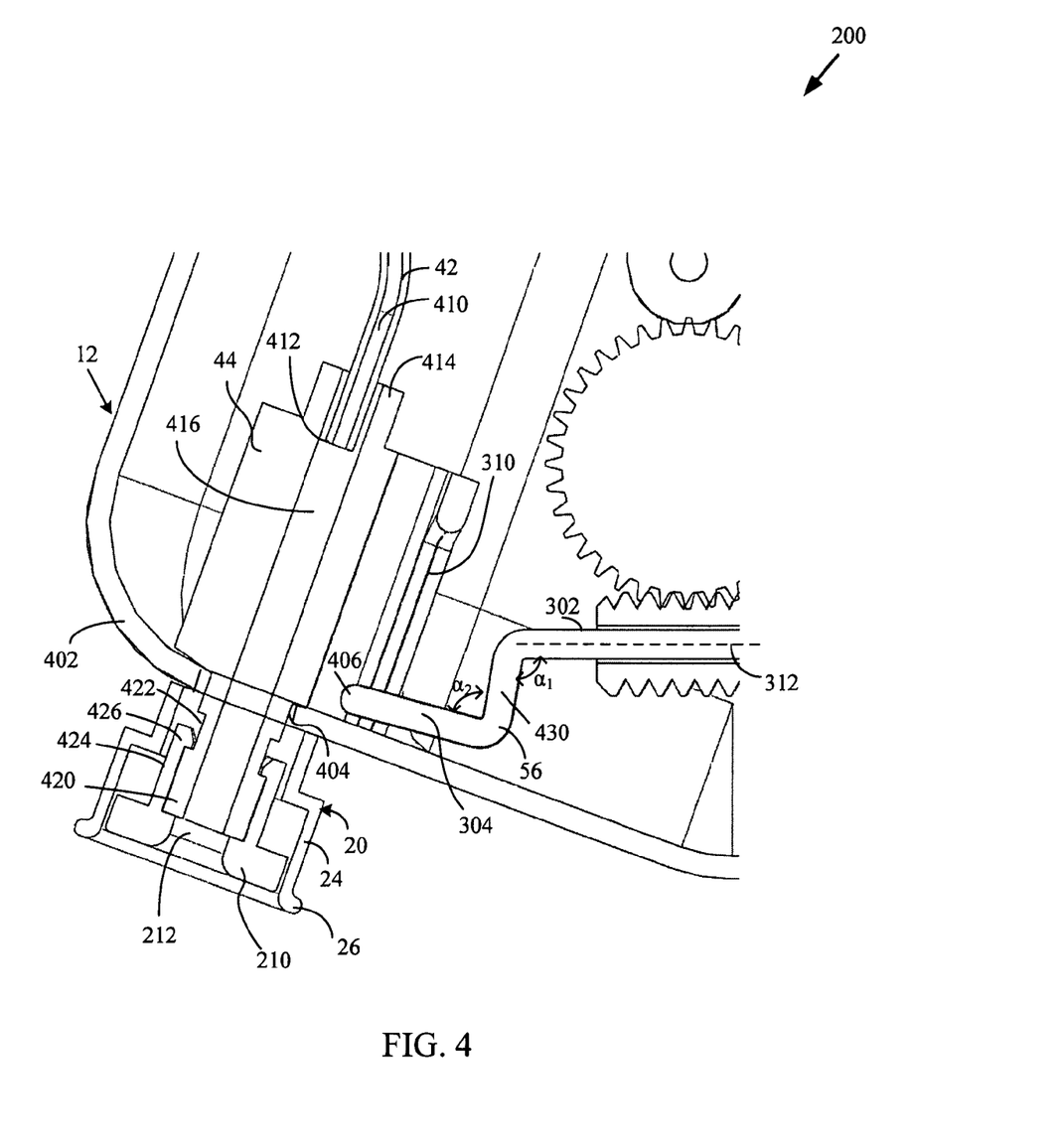
FIG. 4 is a cross-sectional view illustration of a treatment head portion of the microdermabrasion device according to an embodiment of the present invention.

In some embodiments, pump 40 may be actuated by the same system 50 and motor 70 that drives movement of the treatment head 20. For example, pump 40 may be a diaphragm pump as shown in FIGS. 2 and 3. In this example, a piston portion 222 of pump 40 is driven by a connecting rod 60 that is eccentrically and rotatably connected, e.g., at point 62, to a helical gear 58 driven by a spiral gear 54 mounted on rotatable crankshaft 56. In use, as motor rotates reduction gears 250 and 64, spiral gear 54 rotates about the proximal axis of crankshaft 56. The proximal axis 302 of crankshaft 56 is shown in FIG. 4. The teeth of spiral gear 54 engage teeth 358 on helical gear 58, causing gear 58 to eccentrically rotate about axis 62. Rotation of gear 58 drives rod 60 in a reciprocating fashion, which in turn drives piston 222 of pump which is connected to and causes displacement of diaphragm 220 to pump materials from container 30 and through pump 40. The output 37 of pump 40 is connected through a hollow central portion of the oscillating spindle 44 to treatment head 20, e.g., by flexible tube 42. As described above, abrading member 210 of treatment head 20 preferably includes one or more passages 212 through which materials pumped from container 30 may pass. While pump 40 is shown and described as a diaphragm pump, one skilled in the art will appreciate that various other types of pumps may be employed, for example a displacement pump, a reciprocating pump, a positive or negative pressure pump, a bladder, a screw, a syringe, or any other type of pump. In other embodiments, no pump is used, and material from container 30 may be dispensed by applying manual pressure to container. In other embodiments, pump 40 and treatment head 20 may be driven independently. Treatment head 20 may continue to be driven by motor 70 while pump 40 comprises a second motor. This second motor may be powered by power source 80, a secondary power source, or manual pressure.

FIG. 4 shows a cross-sectional side view of treatment head 20, spindle 44 and associated components of device 200 according to one embodiment of the present invention. As described above, spindle 44 preferably includes a hollow portion or passage 416 for flow therethrough of material dispensed from container to treatment head 20. For example, an end 412 of pump output tube 42 is disposed within or otherwise connects or communicates with passage 416 of spindle 44, e.g., through a proximal end 414 of spindle. Passage 416 preferably extends from end 414 of spindle to a distal end 420, to which treatment head 20 attaches such that opening 212 of abrading member 210 communicates with passage 416. In the embodiment shown, abrading member 210 of treatment head is removably attached to end 420 of spindle, which extends from a housing 12 of the device 200. In some embodiments, end 420 extends from housing through a hole or other opening 404 in a wall 402 of the housing 12 of the device 200. For example, opening 404 may be dimensioned to allow spindle 44 to freely oscillate within opening 404 during activation by drive assembly 50.

Guard ring 24, abrading member 210 and/or any other portion of treatment head may be removably or non-removably secured to spindle 44. For example, in the embodiment shown in FIG. 4, one or more snaps, clips or other attachment features 424 are used to removably secure abrading member 210 to end 420 of spindle 44, e.g. by engagement of end 426 of clips 424 into a recess or notch 422 of spindle 44. After use, clips 424 may be disengaged from spindle 44 to remove abrading member 210, e.g., for cleaning or disposal. In some embodiments, guard ring 24 of treatment head 20 secures to wall 402 of housing 404, such that abrading member 210 moves within and with respect to guard ring 24 when spindle 44 is oscillated by drive assembly 50. In other embodiments, guard ring 24 is secured to abrading member 210, such guard ring 24 moves with abrading member 210 when spindle is oscillated or otherwise moved by drive assembly 50.

Also shown in the cross-sectional illustration of FIG. 4 is an example of the engagement between drive assembly 50 and spindle 44 which produces the oscillating movement of abrading member 210. In this embodiment, end 304 of crankshaft 56 extends into spindle 44 through elongated slot 310 in spindle. In some embodiments, tip 406 of crankshaft 56 may include, or have attached thereto, one or more retaining features, springs or other structures (not shown) to hold end 304 of crankshaft 56 within slot 310 and/or to facilitate movement of end 304 within slot 310.

As discussed above, in some embodiments distal portion 304 is offset from and angled with respect to axis 312, e.g., portion 304 and axis 312 are not parallel, such that $\alpha_1 + \alpha_2 \neq 180°$, where $\alpha_1$ is the angle between 304 and transverse member 430 of crankshaft, and $\alpha_2$ is he angle between the axis of rotation of 302 and member 430 of crankshaft 56. Similarly, spindle 44 and treatment head 20 may be angled obliquely with respect to the long axis 312 of crankshaft 302. In some embodiments, proximal end 414 of spindle may be pivotably secured to device, e.g. to housing, pump, or another feature using a bearing surface or other low friction fitting which allows spindle to oscillate or rotate, but not translate. In other embodiments, tube 412 may aid in securing spindle 44.

Figure 5A:
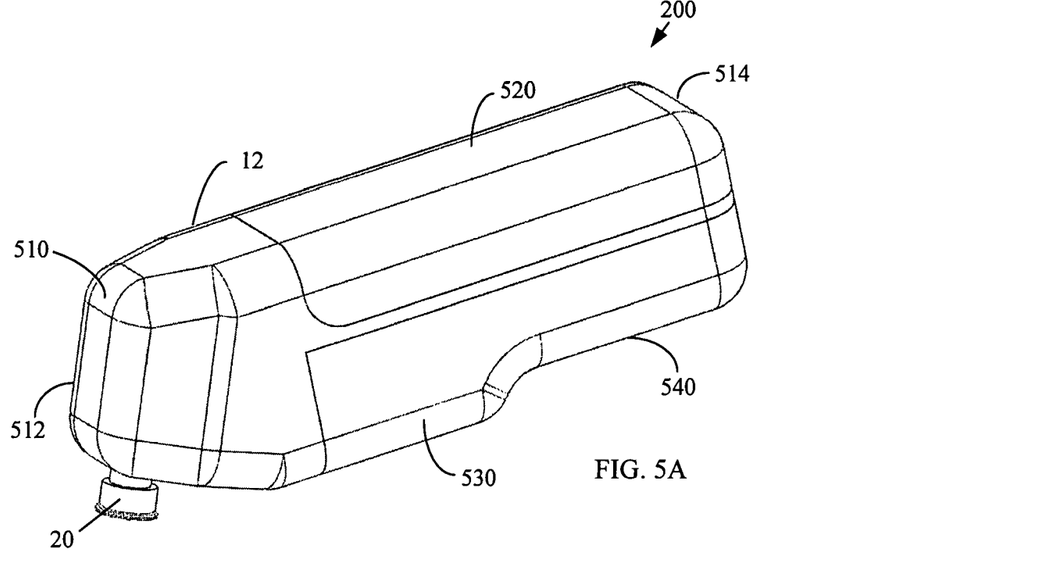
FIGS. 5A and 5B are perspective view illustrations of a microdermabrasion device enclosed in a housing according to an embodiment of the present invention.
Figure 5B:
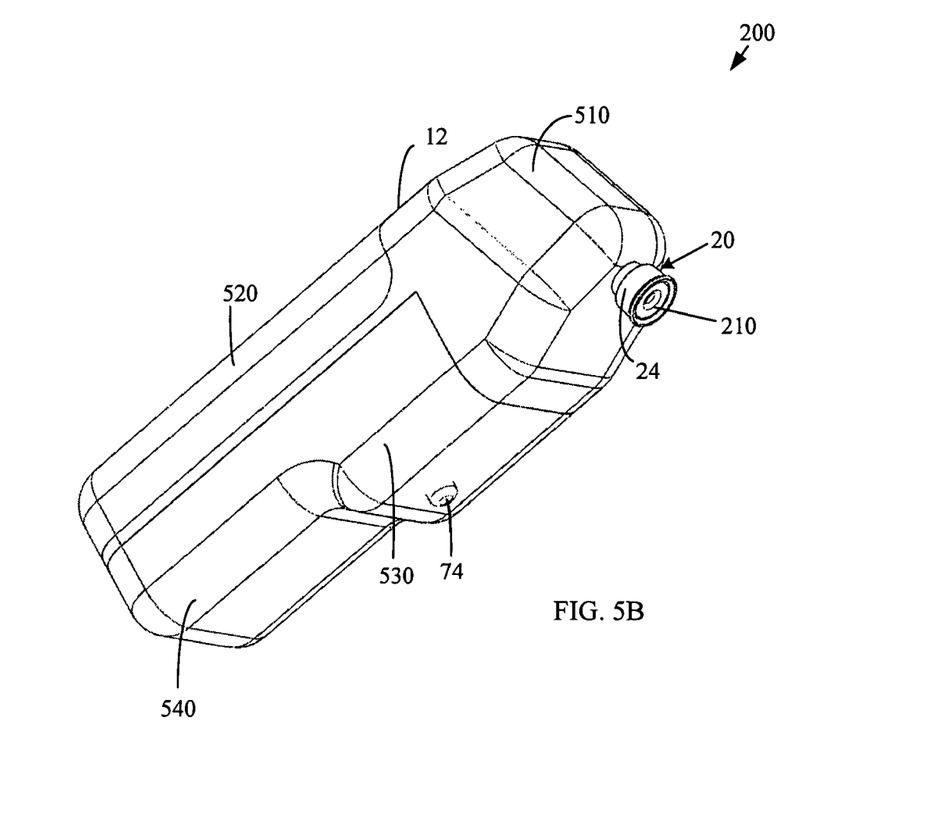

FIGS. 5A and 5B are perspective view illustrations of a microdermabrasion device enclosed in a housing assembly 12 according to an embodiment of the present invention. In one embodiment, housing assembly 12 comprises a main housing 510 which surrounds and encloses components in the distal end 512 of the device 200, including for example, spindle 44, pump 40, and a portion of drive assembly including crankshaft 56, spiral gear 54, coupling 52a and other components distal from coupling 52a (e.g., as shown in FIG. 3). Treatment head 20, including abrading member 210, may extend from a lower surface of main housing 510 as shown in FIG. 5B.

A removable access cover 520 may attach to main housing 510 and provide access to container 30, e.g., to facilitate installation, removal and/or replacement of container 30. A separate electrical sub-housing 530 may enclose electrical components such as power supply and motor, as well as a portion of drive assembly 50, e.g., reduction gearing 250, 64 and coupling 52a. The electrical sub-housing 530 may be removed from the device, for example, during cleaning or to charge the power supply. Electrical switch 74 or button may extend from the electrical sub-housing to allow a user to selectively start or stop the device motor. In some embodiments, a portion of the electrical sub-housing, e.g., near proximal end 514, includes a narrowed or contoured handle portion 540 to facilitate gripping and manipulation of the device 200 by a user.

Figure 6:
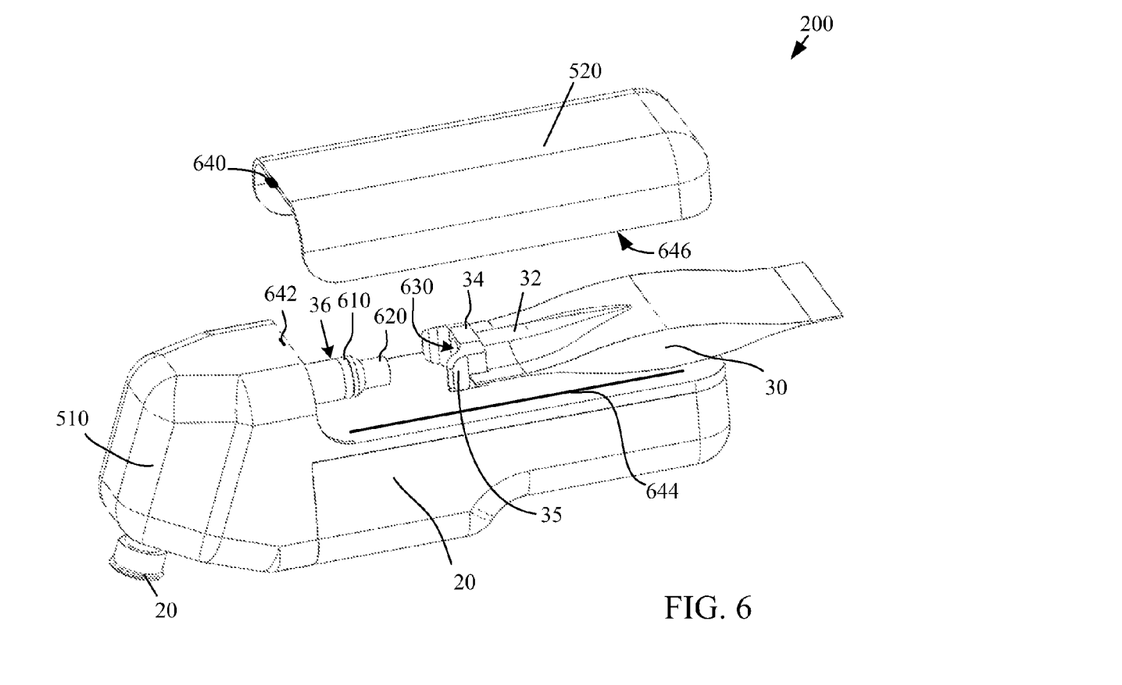
FIG. 6 is a perspective view illustration of the device of FIGS. 5A and 5B, showing an access cover removed.

FIG. 6 is a perspective view illustration of the device of FIGS. 5A and 5B, showing access cover 520 removed and container 30 removed from or unattached to pump input port 36. In some embodiments, input port 36 includes a seal 610, e.g. an o-ring friction fit seal and a nipple 620 or narrow portion adapted to fit through an access port 630 in coupler 34 and into neck 32 of container 30. In some embodiments, port 630 is covered by a breakable seal, e.g. a foil seal, which is broken by nipple 620 when a new container is pressed over nipple and sealingly engaged with port 36. As described earlier, coupler 34 may include any number of flanges 35 or other features to facilitate installation and/or removal of a container. In some embodiments, cover 520 removably attaches to main housing using one or more engagement features, e.g., tab 640 and tab retainer 642, and/or positioning features such as guide 644 which mates with a lower edge 646 of cover 520. Other connectors, fasteners or other engagement features may be used to removably secure cover 520 to main housing 510 or to another portion of device 200.

Figure 7:
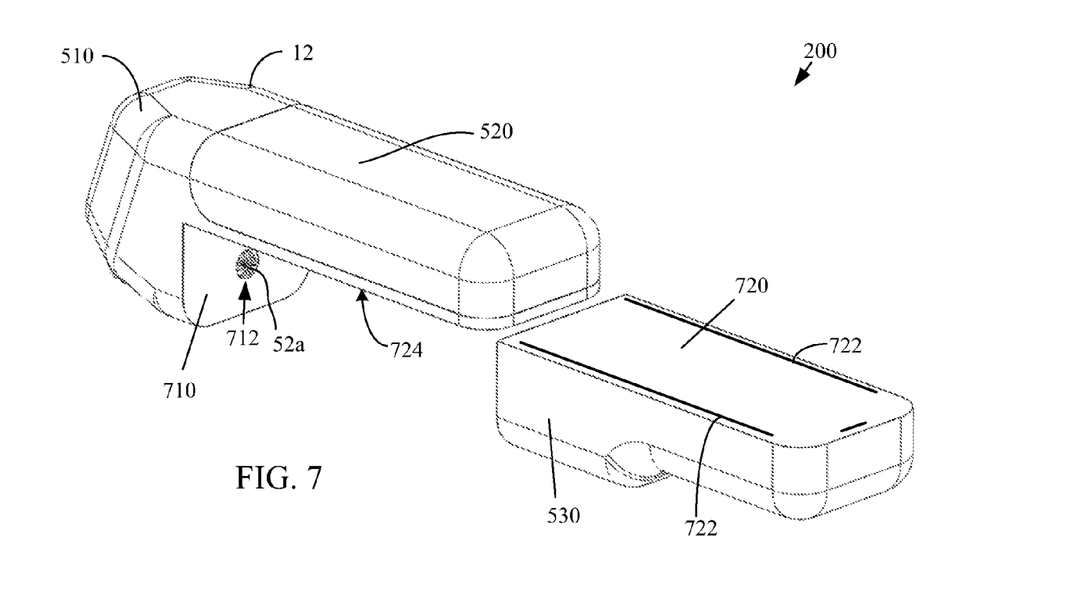
FIG. 7 is a perspective view illustration of the device of FIG. 6, showing an electrical subhousing removed.

FIG. 7 is a perspective view illustration of the device of FIG. 6, showing electrical sub-housing 530 detached from main housing 510. In this example, a surface 710 of main housing 510 includes an access hole 712 through which drive assembly coupling 52a may be engaged by corresponding coupling 52b of electrical sub housing (not shown). Upper surface 720 of electrical sub-housing is configured to mate with a corresponding surface of main housing 724. Electrical sub-housing 530 and/or main housing 510 may include any number and/or type of engagement features to align and secure sub-housing 530 to housing 510.

The above description illustrates various embodiments of the present invention along with examples of how aspects of the present invention may be implemented. The above examples and embodiments should not be deemed to be the only embodiments, and are presented to illustrate the flexibility and advantages of the present invention as defined by the following claims. Based on the above disclosure and the following claims, other arrangements, embodiments, implementations and equivalents will be evident to those skilled in the art and may be employed without departing from the spirit and scope of the invention as defined by the claims.

What is claimed is:

1. A handheld microdermabrasion device, comprising:
an abrading member having abrasive particles on a surface of the abrading member for removing dead cells from a layer of skin of a user;
a housing comprising:
a drive system comprising:
a motor,
a crankshaft, wherein said motor is coupled with said abrading member through the crankshaft and said motor and said crankshaft are configured to drive movement of the abrading member,
a first gear coupled to the crankshaft, and
a second gear,
a fluid delivery system fluidly connected to an interface between the abrading member and the skin of a user, wherein said fluid delivery system contains a skin treatment fluid, and said fluid delivery system comprising:
a pump mechanism to deliver the skin treatment fluid to the interface between the abrading member and the skin of the user, wherein the second gear is coupled to the pump mechanism and the second gear is driven by the first gear to actuate said pump mechanism;
a power source in electrical communication with said drive system for activating said drive system,
wherein said housing encapsulates within the housing said pump mechanism, said fluid delivery system, said drive system, and said power source, wherein said abrading member extends outward from the housing.

2. The device of claim 1, wherein the pump mechanism comprises a pump.

3. The device of claim 2, further comprising an input port communicating with said pump.

4. The device of claim 3, further comprising a container removably coupled with the input port.

5. The device of claim 4, wherein the container comprises a wall surrounding a central cavity for containing a material.

6. The device of claim 5, wherein the container wall comprises a plastic sheet, a metal foil, or a combination thereof, and is at least partially collapsible as said material is dispensed from the container.

7. The device of claim 4, wherein said container contains said skin treatment fluid.

8. The device of claim 1, wherein said drive system further comprises one or more third gears for driving the movement of the abrading member.

9. The device of claim 8, wherein said drive system further comprises a spindle coupled with said abrading member and pivotably attached within said housing, said spindle for guiding the movement of the abrading member.

10. The device of claim 9, wherein said crankshaft has a proximal end coupled with the one or more third gears and a distal end slidably engaged within a slot in the spindle, wherein rotating the crankshaft slides the distal end of the crankshaft within the slot and moves the abrading member in a defined pattern.

11. The device of claim 1, wherein said drive system is configured to drive both the abrading member and the pump mechanism to deliver the skin treatment fluid to the interface between the skin of the user and the abrading member.

12. The device of claim 1, further comprising a guard ring laterally surrounding said abrading member.

13. The device of claim 1, wherein said abrading member comprises an annulus including a central opening coupled to said fluid delivery system for passing said skin treatment fluid therethrough.

14. The device of claim 1, wherein:
the first gear is mounted on the crankshaft and causes rotation of the second gear when the crankshaft is rotated; and
the rotation of the second gear causes displacement of a diaphragm to pump the skin treatment fluid to the interface.

15. A handheld microdermabrasion device, comprising:
an abrading member having abrasive particles on a surface of the abrading member for removing dead cells from a layer of skin of a user;
a housing comprising:
- a drive system, said drive system coupled with said abrading member and configured to drive movement of the abrading member;
- a fluid delivery system fluidly connected to an interface between the abrading member and the skin of the user, wherein said fluid delivery system contains a skin treatment fluid, and said fluid delivery system comprising:
  - a pump mechanism to deliver the skin treatment fluid to the interface between the abrading member and the skin of the user, wherein the pump mechanism comprises a syringe and a spring mechanism abutted to the syringe, and wherein the spring mechanism comprises a compressed state and an uncompressed state,
- a power source in electrical communication with said drive system for activating said drive system,
wherein said housing encapsulates within the housing said pump mechanism, said fluid delivery system, said drive system, and said power source, wherein said abrading member extends outward from the housing.

16. The device of claim 15, wherein the syringe comprises a plunger and a syringe chamber filled with said skin treatment fluid.

17. The device of claim 16, wherein the plunger is abutted to the spring mechanism.

18. The device of claim 16, wherein the syringe chamber is filled with an air pocket having a volume greater than the volume of a tube coupled between the syringe and the abrading member.

19. A method of performing microdermabrasion, comprising:
applying an abrading member of a handheld microdermabrasion device to a skin surface, the abrading member having abrasive particles on a surface of the abrading member for removing dead cells from a layer of the skin surface, said microdermabrasion device including a housing, said housing encapsulating within the housing a power supply, a fluid delivery system containing a skin treatment solution and a pump mechanism to deliver said skin treatment solution, and a drive system including a motor, crankshaft, a first gear coupled to the crankshaft, and a second gear coupled to the pump mechanism;
driving the crankshaft with the motor, wherein the driving of the crankshaft causes oscillation of the abrading member over the skin surface using the drive system; and
driving the first gear via the driving of the crankshaft, the second gear being driven by the first gear to actuate said pump mechanism to apply said skin treatment solution from the fluid delivery system within the microdermabrasion device to the skin.

20. The method of claim 19, wherein the pump mechanism includes a pump, wherein said applying further comprises attaching a container to an input port of said pump, and using the drive system to both actuate the pump to deliver the skin treatment solution from the container and actuate the abrading member.

21. A method of performing microdermabrasion, comprising:
applying an abrading member of a handheld microdermabrasion device to a skin surface, the abrading member having abrasive particles on a surface of the abrading member for removing dead cells from a layer of the skin surface, said microdermabrasion device including a housing, said housing encapsulating within the housing a power supply, a fluid delivery system containing a skin treatment solution and a pump mechanism to deliver said skin treatment solution, and a drive system coupled with the abrading member;
oscillating the abrading member over the skin surface using the drive system, wherein the pump mechanism includes a syringe between a spring mechanism and a tube, wherein said applying further comprises attaching the syringe between the spring mechanism and the tube, the syringe comprising a syringe chamber filled with said skin treatment fluid, and actuating the spring mechanism to force the skin treatment fluid from the syringe chamber, through the tube, and to an interface between the skin of a user and the abrading member; and
applying said skin treatment solution from the fluid delivery system within the microdermabrasion device to the skin.

* * * * *